United States Patent [19]

Horák et al.

[11] Patent Number: 4,622,367
[45] Date of Patent: Nov. 11, 1986

[54] X-RAY CONTRAST SPHERICAL HYDROGEL PARTICLES BASED ON POLYMER AND COPOLYMERS OF ACRYLATES AND METHACRYLATES AND THE METHOD FOR PREPARATION THEREOF

[75] Inventors: Daniel Horák; Marie Metalová, both of Prague; Frantisek Svec, Hrebec; Jaroslav Drobník; Jaroslav Kálal, both of Prague, all of Czechoslovakia; Michail I. Kuzin, Moscow, U.S.S.R.; Arnold A. Adamian, Moscow, U.S.S.R.; Jurij V. Moiseiev, Moscow, U.S.S.R.; Klara Z. Gumargalieva, Moscow, U.S.S.R.

[73] Assignee: Ceskoslovenska akademie ved, Czechoslovakia

[21] Appl. No.: 807,281

[22] Filed: Dec. 10, 1985

[30] Foreign Application Priority Data

Dec. 12, 1984 [CS] Czechoslovakia ............ 9654-84

[51] Int. Cl.$^4$ ............................................. C08F 8/32
[52] U.S. Cl. .................................. 525/381; 525/379; 525/382; 524/238; 524/239; 428/402
[58] Field of Search ............... 524/239, 238; 428/402; 525/379, 381, 382

Primary Examiner—Paul R. Michl
Assistant Examiner—Alex H. Walker
Attorney, Agent, or Firm—Leydig, Voit & Mayer

[57] ABSTRACT

The invention pertains to X-ray contrast spherical hydrogel particles based on polymers and copolymers of acrylates and methacrylates and to a method of their preparation.

The subject of this invention are X-ray contrast spherical hydrogel particles based on polymers and copolymers of acrylates and methacrylates characterized by the particles of spherical form with diameter 0.2 to 2 mm, which strongly swell in water and contain a derivative of amino-triiodobenzoic acid of general formula I,

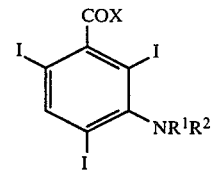

where $R^1, R^2$ is hydrogen, acyl group with 1 to 3 carbon atoms or alkyl with 1 to 10 carbon atoms and X is halogen, —OH or —NH(CH$_2$)$_n$NH$_2$, where n=1-6, covalently bonded to the polymer skeleton.

A method for preparation of X-ray contrast hydrogel particles according to the invention in which hydrogel particles, containing hydroxyl or epoxide groups localized on side chains of the polymer skeleton, are allowed to swell in an excess of a solvent chosen from the group comprising dioxane, dimethylacetamide, dimethylformamide, tetrahydrofuran and dimethylsulfoxide, which contains the dissolved derivative of amino-triiodobenzoic acid of the general formula I, optionally together with a compound reacting with hydrogen halogenide formed, which is selected, for example, from the group comprising tertiary amines, the dispersion is heated to 100° C. at utmost and allowed to react for 150 hours at utmost, the solid phase is separated and freed of soluble substances by washing.

The procedure according to the invention provides spherical hydrogels with X-ray contrast properties without changing their other properties substantial for application in medical practice.

2 Claims, No Drawings

X-RAY CONTRAST SPHERICAL HYDROGEL PARTICLES BASED ON POLYMER AND COPOLYMERS OF ACRYLATES AND METHACRYLATES AND THE METHOD FOR PREPARATION THEREOF

The invention pertains to X-ray contrast spherical hydrogel particles based on polymers and copolymers of acrylates and methacrylates and to a method for their preparation.

Hydrophilic gels, based above all on polymers and copolymers of 2-hydroxyethyl methacrylate, some other esters of methacrylic acid, methacrylamide, acrylamide and their derivatives, are used as materials for prostheses in medicine. Methods of their preparation, either in a compact form or a porous form, are described and protected by numerous patents. One of possible applications of hydrogels are emboluses for the vascular occlusion.

The emboluses for vascular occlusion are known in the recent medical practice. Till now, the particles used have been made from various materials including metals (gold, platinum), ceramics, glass, and also synthetic or natural polymers. In contrast to the former ones, polymeric emboluses have an indisputible advantage in their better biocompatibility towards patient's tissues, they are able to keep the formed thrombos and are very fast encapsulated. However, the synthetic methods known for the present give emboluses in the form of cylinder and are obtained by cutting of longer rods made mainly from a hydrogel. The polymerization is carried out in bulk, i.e. a mold is charged with a monomer or monomers containing the dissolved initiator and the polymerization reaction is started by increasing temperature. After the reaction period a hard plug of required diameter is obtained. The cylindric emboluses are admissible in medical practice, but they have to be absolutely precisely oriented in the place of occlusion for their correct location. This shortcoming is overcome by spherical emboluses, which are regular and need not be oriented. However, the above decribed polymerization in bulk cannot be used for their production. One of possible ways is the suspension polymerization, which directly leads to spherical particles with the diameter controllable to certain extent by choosing the reaction conditions.

It is often desirable to check the position of an implant in body of the patient or during its introduction by X-ray. The existing patents describe the preparation of X-ray contrast hydrogels by dissolution of a X-ray contrast substance in a polymerization mixture, which substance is insoluble in water and precipitates as a solid in the gel mass after swelling of hydrogel with water (Czechoslovak Patent Application No. 6133-83). Another method uses a precipitate of AgI, AgI$_3$ or AgI$_n$, where n>3, as the X-ray contrast substance present in hydrogel, which are prepared by the reaction of two water-soluble compounds directly in the hydrogel in such a way, that the hydrogel swelled with an aqueous solution of one of these compounds is immersed into a solution of the other compound and, after precipitation of the X-ray contrast substance, water-soluble compounds are removed from the hydrogel by washing with water (Czechoslovak Patent Application No. 6134-83). Both these procedures cannot be used for hydrogels for spherical form prepared by suspension polymerization. In the first case, addition of the X-ray contrast substances into a polymerization mixture damages the stability of suspension and the resulting polymer has not the form of spheres but the form of an agglomerate. In the latter case, liberation of the X-ray contrast substance occurs into the patient's body because the X-ray contrast substance is not chemically bonded to the hydrogel. These shortcomings are overcome by a method for preparation of X-ray contrast particles according to the invention.

The subject of the invention are X-ray contrast spherical hydrogel particles based on polymers and copolymers of acrylates and methacrylates, which particles are characterized by a spherical form with diameter 0.2 to 2 mm, strongly swell in water and contain the derivative of amino-triiodobenzoic acid of general formula I,

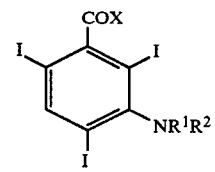

where R$^1$ and R$^2$ is hydrogen, acyl group with 1 to 3 carbon atoms, or alkyl with 1 to 10 carbon atoms and X is halogen, —OH or —NH(CH$_2$)$_n$NH$_2$, where n=1-6, covalently linked to a polymer skeleton.

A method for preparation of the X-ray contrast hydrogel particles according to the invention consists in swelling of hydrogel particles, containing hydroxyl or epoxide groups localized on side chains of the polymer skeleton, in an excess of a solvent chosen from the group comprising dioxane, dimethylacetamide, dimethylformamide, tetrahydrofuran, and dimethylsulfoxide, which contains the dissolved derivative of amino-triiodobenzoic acid of general formula I, optionally together with a compound reacting with hydrogen halogenide formed, which is chosen, for example, from the group comprising tertiary amines, the dispersion is heated to 100° C. at utmost and allowed to react for 150 hours at utmost, the solid phase is separated and freed of soluble substances by washing.

In this procedure, reactive groups of the suspension polymer—spherical particles of the hydrogel, which is crosslinked with up to 5% of a bifunctional monomer, undergo the chemical reaction with the X-ray contract substance. Such organic compounds are used as X-ray contrast substances which are able to react, for example, with hydroxyl groups of 2-hydroxyethyl methacrylate units in hydrogel or with other reactive groups of polymers. Advantageously, the compound of general formula II,

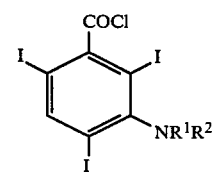

where R$^1$,R$^2$ is hydrogen, acyl group with 1 to 3 carbon atoms or alkyl with 1 to 10 carbon atoms, which is prepared from the compound of general formula III,

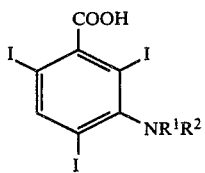

where $R^1, R^2$ have the above mentioned meaning, or the compound of general formula IV,

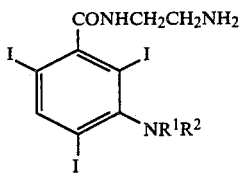

where $R^1, R^2$ have the same meaning, which is prepared from the compound II, are used as the X-ray contrast substance.

The reaction according to the invention is carried out in such a way, that a sufficient amount of the reactive X-ray contrast compound is dissolved in a polar aprotic solvent and spherical particles of hydrogel, which is not contrast to X-ray, are allowed to swell in this solution and to react while immersed in this solution for certain time at elevated temperature. The reaction may be advantageously sped up with an agent removing the formed hydrogen chloride.

For example, triethylamine, pyridine, and the like, can be used as the agent removing hydrogen chloride. In principle, any solvent which dissolves but does not react with the X-ray contrast compound can be used, but it is of advantage to use in practice such solvents which swell the hydrogel at the same time, i.e., for example, dioxane, dimethylacetamide, dimethylformamide, tetrahydrofuran, dimethylsulfoxide, etc.

The resulting X-ray contrast polymer is washed after reaction with a suitable solvent until all low-molecular-weight substances are completely removed.

The method according to the invention enables to obtain spherical hydrogels with X-ray contrast properties without changing their other properties which are substantial for application in medical practice. The contrast in X-ray is pronounced to such extent that also implants of small dimensions can be visualized, for example, so called artificial emboluses with the size below 1 mm. The X-ray contrast spherical hydrogels are marked for their high stability of opacity degree after implantation into a tissue of living organism and, consequently, may be advantageously used in the cases when it is desirable to follow the implant for a longer period of time after its surgical or other introduction.

The method of contrasting is commonly applicable not only for the spherical hydrogel particles, but also for synthetic polymer particles of other form prepared by other than suspension technique.

EXAMPLE 1

A polymerization reactor of volume 250 ml was charged with 25 ml of a mixture consisting of 9.8 ml of 2-hydroxyethyl methacrylate, 0.2 ml of ethylene dimethacrylate, 0.1 ml of 2,2'-azobis(isobutyronitrile), 7.5 ml of cyclohexanol and 7.5 ml of 1-dodecanol. Into this mixture, 75 ml of 1% aqueous solution of poly(vinylpyrrolidone) (K-value 90, mol. wt. 360,000 was added, oxygen was removed by bubbling an inert gas through the mixture, and the reactor was sealed. A horse-shoe stirrer was run at 100-150 r.p.m., the mixture was heated to 70° C. by a heating jacket, and polymerization was carried out for 10 hours. After completion, the resulting particles were repeatedly washed with water and ethanol to remove unreacted monomers and the suspension stabilizer, and dried. Dry spherical particles were classified on screens into narrow fractions according to their size in the region 0.2-2 mm. A part (20 g) of these particles was swelled and immersed into a solution of 20 g of 3-acetylamino-2,4,6-triiodobenzoyl chloride in 60 ml of dry dioxane, 5.3 ml of triethylamine was added and the mixture was shaken in a thermostated bath at 60° C. for 150 hours. The spheres were then washed in dioxane and in boiling water, which was changed every day. The extract from spheres was checked by UV spectrometry. The washed spheres were dried. An elemental analysis revealed that the particles contain 29.1 wt.-% of bonded iodine.

The spheres were sterilized and implanted to patients in occlusion of bronchial, renal, mesenteric, underbelly and other arteries to stop bleeding into internal organs and in endovascular embolism for the treatment of non-malignant tumors from vessels arising by evolutional defects.

EXAMPLE 2

The particles were prepared according to example 1 with the distinction that 3-amino-2,4,6-triiodobenzoyl chloride was used as the X-ray contrast substance in the same amount. Elemental analysis revealed that the particles contained 26.6 wt.-% of bonded iodine.

EXAMPLE 3

Starting particles were obtained by the suspension radical polymerization according to example 1 using glycidyl methacrylate instead of 2-hydroxyethyl methacrylate. X-ray contrast hydrogels were prepared similarly as in example 1, with the distinction that 0.1 g of spherical particles of glycidyl methacrylate-ethylene dimethacrylate copolymer was swelled in a solution of 0.6 g of 2-aminoethylamide of 3-amino-2,4,6-triiodobenzoic acid in 8 ml of distilled dimethylformamide under otherwise identical conditions. Elemental analysis revealed that the particles contained 13.4 wt.-% of bonded iodine.

EXAMPLE 4

The particles were prepared according to example 3, with the distinction that 2-aminoethylamide of 3-acetylamino-2,4,6-triiodobenzoic acid was used as the reactive X-ray contrast compound. Elemental analysis revealed that the particles contained 13.6 wt.-% of bonded iodine.

We claim:

1. X-ray contrast spherical hydrogel particles based on polymers and copolymers of acrylates and methacrylates, wherein particles have the form of spheres with diameter 0.2 to 2 mm, strongly swell in water, and contain a derivative of amino-triiodobenzoic acid of general formula I,

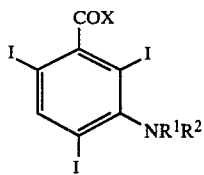

where $R^1$ and $R^2$ is hydrogen, acyl group with 1 to 3 carbon atoms, or alkyl with 1 to 10 carbon atoms and X is halogen, —OH or —$NH(CH_2)_nNH_2$, where $n=1–6$, covalently bonded to the polymer skeleton.

2. Method for preparation of X-ray contrast hydrogel particles according to claim 1, wherein hydrogel particles, containing hydroxyl or epoxide groups localized on side chains of the polymer skeleton, are allowed to swell in an excess of a solvent, selected from the group comprising dioxane, dimethyl acetamide, dimethylformamide, tetrahydrofuran and dimethylsulfoxide, which contains the dissolved derivative of amino-triiodobenzoic acid of general formula I, optionally together with a compound reacting with hydrogen halogenide formed, and selected, for example, from the group comprising tertiary amines, the dispersion is heated to 100° C. at utmost and allowed to react for 150 hours at utmost, the solid phase is separated and freed of soluble substances.

* * * * *